(12) United States Patent
Schmid et al.

(10) Patent No.: US 11,116,396 B2
(45) Date of Patent: Sep. 14, 2021

(54) IMAGING MULTIPLE PARTS OF THE EYE

(71) Applicant: Novartis AG, Basel (CH)

(72) Inventors: Stefan Schmid, Neuendettelsau (DE); Berndt Warm, Schwaig (DE)

(73) Assignee: Alcon Inc.

( * ) Notice: Subject to any disclaimer, the term of this patent is extended or adjusted under 35 U.S.C. 154(b) by 53 days.

(21) Appl. No.: 16/213,321

(22) Filed: Dec. 7, 2018

(65) Prior Publication Data

US 2019/0183336 A1    Jun. 20, 2019

Related U.S. Application Data

(60) Provisional application No. 62/607,661, filed on Dec. 19, 2017.

(51) Int. Cl.
| | | |
|---|---|---|
| *A61B 3/14* | (2006.01) | |
| *A61B 3/00* | (2006.01) | |
| *A61B 3/10* | (2006.01) | |
| *G02B 3/00* | (2006.01) | |
| *A61B 3/12* | (2006.01) | |
| *A61B 3/117* | (2006.01) | |

(52) U.S. Cl.
CPC .............. *A61B 3/14* (2013.01); *A61B 3/0008* (2013.01); *A61B 3/117* (2013.01); *A61B 3/12* (2013.01); *G02B 3/0006* (2013.01)

(58) Field of Classification Search
CPC ......... G02B 5/201; A61B 3/14; A61B 3/1225; A61B 3/1015; A61B 3/10; A61B 3/12; A61B 3/107; A61B 3/117; A61B 3/103; A61B 3/113

USPC ........ 351/206, 200, 205, 209–210, 221, 246
See application file for complete search history.

(56) References Cited

U.S. PATENT DOCUMENTS

| | | | |
|---|---|---|---|
| 2012/0182438 A1* | 7/2012 | Berkner ................ | G01J 3/2823 348/222.1 |
| 2012/0268717 A1 | 10/2012 | Zhou | |
| 2013/0010260 A1 | 1/2013 | Tumlinson | |
| 2016/0278637 A1 | 9/2016 | Gao et al. | |
| 2017/0105615 A1 | 4/2017 | Gao | |
| 2018/0228368 A1* | 8/2018 | Massie .................. | A61B 3/125 |

OTHER PUBLICATIONS

"Mikro-Objektivlinsen auf CMOS-Chips [Micro-objective lenses on CMOS chips]." Markt & Technik. No. 13/2017. p. 26.

* cited by examiner

*Primary Examiner* — Dawayne Pinkney

(57) ABSTRACT

A lens-sensor array for imaging parts of an eye comprises a lens array disposed onto a sensor array. The lens array transmits a light from a lens towards the sensor array. The lens array comprises a first section configured to direct the light reflected by a first part of the eye to the sensor array, and a second section configured to direct the light reflected by a second part of the eye to the sensor array. The first section comprises first sub-sections, each first sub-section comprising at least one first lenslet. The second section comprises second sub-sections, each second sub-section comprising at least one second lenslet. The sensor array comprises sensors that detect the light from the lens array and generate sensor signals corresponding to the light reflected by the first part of the eye and the light reflected by the second part of the eye.

7 Claims, 5 Drawing Sheets

IMAGING MULTIPLE PARTS OF THE EYE

PRIORITY CLAIM

This application claims the benefit of priority of U.S. Provisional Patent Application Ser. No. 62/607,661 titled "IMAGING MULTIPLE PARTS OF THE EYE," filed on Dec. 19, 2017, whose inventors are Stefan Schmid and Berndt Warm, which is hereby incorporated by reference in its entirety as though fully and completely set forth herein.

TECHNICAL FIELD

The present disclosure relates generally to surgical devices, and more specifically to imaging multiple parts of the eye.

BACKGROUND

Imaging an object involves detecting light reflected from the object and creating an image of the object from the detected light. During diagnostic and surgical procedures, the eye can be imaged with a variety of techniques. For example, light rays reflected from the cornea can be used to image the cornea. As another example, a wavefront reflected from the retina can be used to image the retina.

BRIEF SUMMARY

In certain embodiments, a system for imaging parts of an eye comprises a light source and optics, a lens, and a lens-sensor array. The light source and optics direct light towards parts of the eye, which reflect the light. The lens transmits the reflected light. The lens-sensor array comprises a lens array disposed onto a sensor array. The lens array transmits a light from a lens towards the sensor array. The lens array comprises a first section configured to direct the light reflected by a first part of the eye to the sensor array, and a second section configured to direct the light reflected by a second part of the eye to the sensor array. The first section comprises first sub-sections, each first sub-section comprising at least one first lenslet. The second section comprises second sub-sections, each second sub-section comprising at least one second lenslet. The sensor array comprises sensors that detect the light from the lens array and generate sensor signals corresponding to the light reflected by the first part of the eye and the light reflected by the second part of the eye.

In certain embodiments, a lens-sensor array for imaging parts of an eye comprises a lens array disposed onto a sensor array. The lens array transmits a light from a lens towards the sensor array. The lens array comprises a first section configured to direct the light reflected by a first part of the eye to the sensor array, and a second section configured to direct the light reflected by a second part of the eye to the sensor array. The first section comprises first sub-sections, each first sub-section comprising at least one first lenslet. The second section comprises second sub-sections, each second sub-section comprising at least one second lenslet. The sensor array comprises sensors that detect the light from the lens array and generate sensor signals corresponding to the light reflected by the first part of the eye and the light reflected by the second part of the eye.

In certain embodiments, a method for making a lens-sensor array for imaging parts of an eye includes providing a sensor array as a substrate. Lens layers are printed onto the substrate to yield a first section that directs the light reflected by a first part of the eye to the sensor array, and a second section that directs the light reflected by a second part of the eye to the sensor array. The first section comprises first sub-sections, each first sub-section comprising at least one first lenslet. The second section comprises second sub-sections, each second sub-section comprising at least one second lenslet.

BRIEF DESCRIPTION OF THE DRAWINGS

Embodiments of the present disclosure are described by way of example in greater detail with reference to the attached figures, in which.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
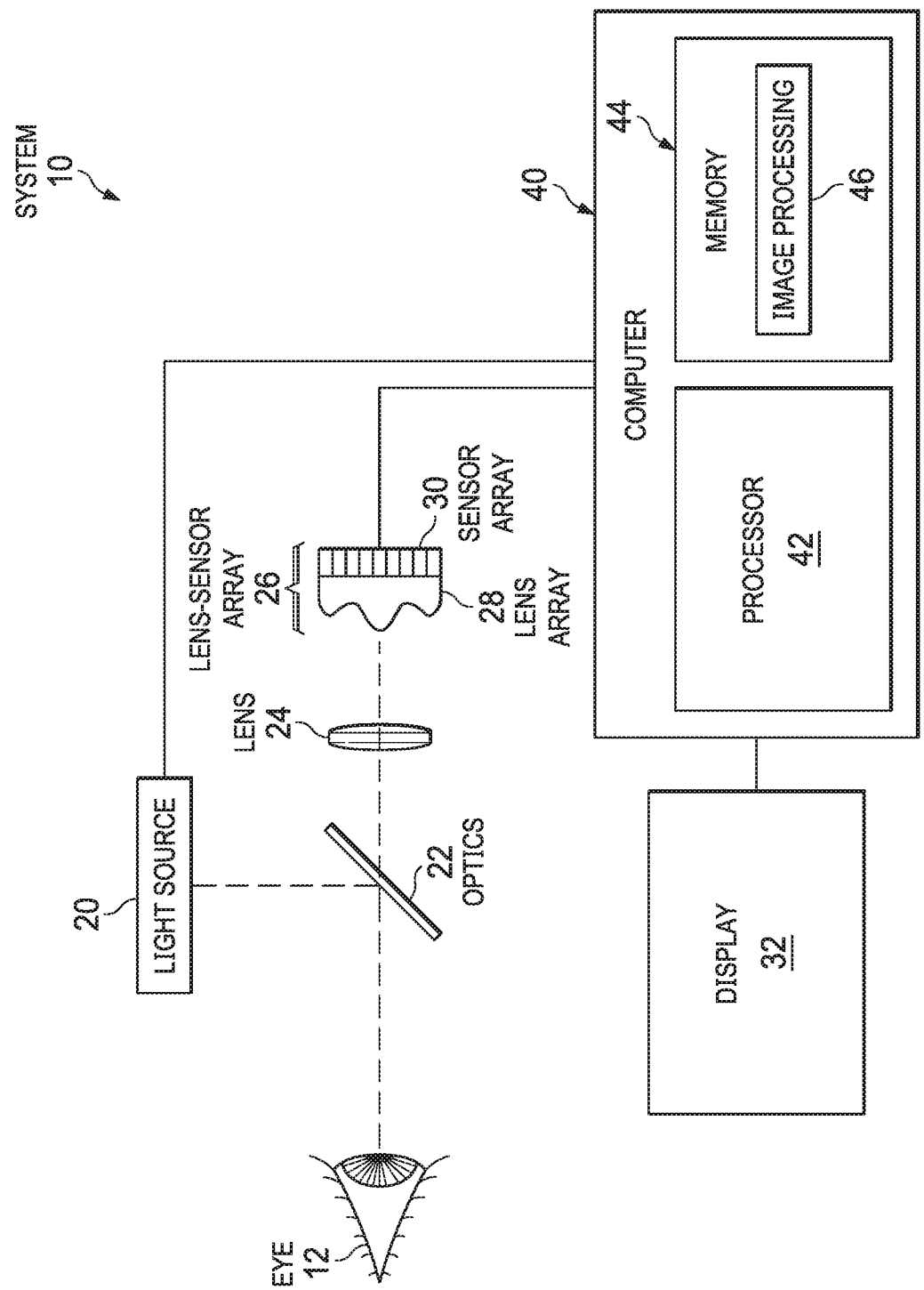
FIG. 1 illustrates an example of a system for imaging parts of an eye.

FIG. 1 illustrates an example of a system 10 for imaging parts of an eye 12. System 10 includes a lens-sensor array that has a lens array disposed onto a sensor array. The lens array comprises first and second sections, where each section is used to simultaneously image different parts of eye 12. For example, the first section may transmit light reflected from the cornea to the sensor array in order to image the cornea, and the second section may transmit a wavefront reflected from the retina to the sensor array in order to image the retina.

As an overview of system 10, in the illustrated example, system 10 comprises a light source 20, optics 22, a lens 24, a lens-sensor array 26 (which comprises a lens array 28 and a sensor array 30), a display 31, and a computer 40 (which comprises one or more processors 42 and one or memories 44, which store an image processing application 46). As an overview of operation of the illustrated example, light source 20 and optics 22 direct light towards parts of eye 12, which reflect the light. Lens 24 transmits the light towards lens-sensor array 26. A first section of lens array 28 directs light reflected from a first part of eye 12 towards sensor array 30, and a second section of lens array 28 directs light reflected from a second part of eye 12 towards sensor array 30 in order to generate images of both parts of eye 12 on display 32. Computer 40 controls the operation of the components of system 10 to generate the images.

In more detail, in the illustrated example, one or more light sources 20 generate light to be directed towards eye 12. Any suitable light source (e.g., a laser or diode, such as a super-luminescent diode (SLED)) generating any suitable light (e.g., infrared or visible light) may be used. As examples, a laser or SLED may illuminate the retina; an incoherent light source (e.g., a set of diodes) may illuminate the eye; and/or an infrared source may illuminate areas to generate an image highlighting blood vessels.

Optics 22 include one or more optical devices that direct the light generated by light source 20 towards parts of eye 12. An optical device transmits, reflects, and/or refracts light. Examples of optical devices include a lens, beam splitter, and mirror. For example, optics 22 may include a splitter that reflects light towards eye 12 and transmits light reflected from eye 12 to lens 24. The parts of eye 12 reflect the light. Examples of parts of eye 12 include the cornea, iris, sclera, crystalline lens, and retina.

Lens 24 is an optical device that transmits the reflected light towards lens-sensor array 26. Lens 24 may have any suitable focal length $f_L$, which may be in the range of 50 to 200, 200 to 400, or 400 to 550 millimeters (mm). Lens 24 may comprise one lens or a system of multiple lenses, e.g., a system with delay lines.

Lens-sensor array 26 comprises lens array 28 disposed onto sensor array 30. Lens array 28 may be disposed onto sensor array 30 using a 3D printing additive manufacturing process, such as two-photon polymerization. In the process, two photons from a red femtosecond laser pulse are absorbed in a photoresist of sensor array 30 and act like a blue photon. This initiates a crosslinking process in a liquid photo-resin. Lens array 28 structure is printed on sensor array 30 layer by layer.

Lens array 28 comprises first and second sections that are used to image different parts of eye 12. A first section of lens array 28 directs light reflected from a first part of eye 12 towards sensor array 30, and a second section of lens array 28 directs light reflected from a second part of eye 12 towards sensor array 30 in order to generate images of both parts of eye 12 on display 32. Each section comprises subsections that have lenslets. The first section comprises first sub-sections, and each first sub-section has at least one first lenslet. The second section comprises second sub-sections, and each second sub-section has at least one second lenslet. In certain embodiments, the first section may be used to image the cornea and other parts of eye 12 near the cornea, e.g., theسclera and iris, and the second section may be used to image the retina and other parts of eye 12 near the retina. The first and section sections are described in more detail with reference to FIG. 2D.

Sensor array 30 comprises sensors that detect the light from lens array 30 and generate sensor signals corresponding to the detected light. The sensor signals can be used to generate images of parts of eye 12. Examples of sensor array 30 include charge-coupled device (CCD) and complementary metal-oxide semiconductor (CMOS) image sensors. Sensor array 30 may have any suitable size and shape. Typical sensor arrays are rectangles with dimensions of less than 10 millimeters (mm).

Computer 40 controls the operation of the components of system 10 to generate the images of parts of eye 12. In certain embodiments, computer 40 instructs light source 20 to generate the light. Computer 40 also receives sensor signals from sensor array 30. Image processing application 46 processes the signals to generate image signals that instructs display 32 to present an image. For example, image processing application 46 filters, pads, and transforms the information received in sensor signals in order to generate the image signals.

Display 32 receives the image signals from computer 40 and displays an image of the parts of eye 12. Display may be any suitable device that can display a digital image (e.g., a computer display, a television screen, or a heads-up display).

Figure 2A:
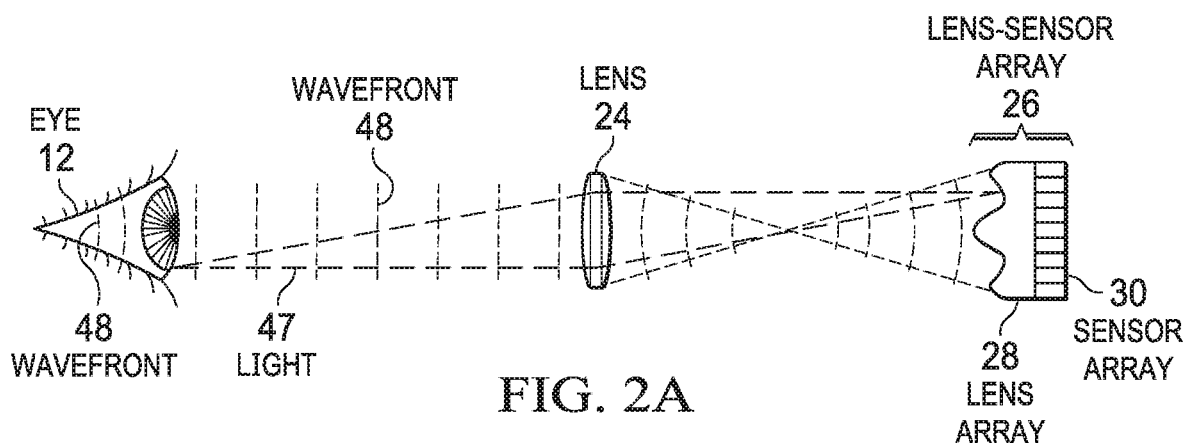
FIG. 2A illustrates imaging the cornea and retina with the system of FIG. 1.
Figure 2B:
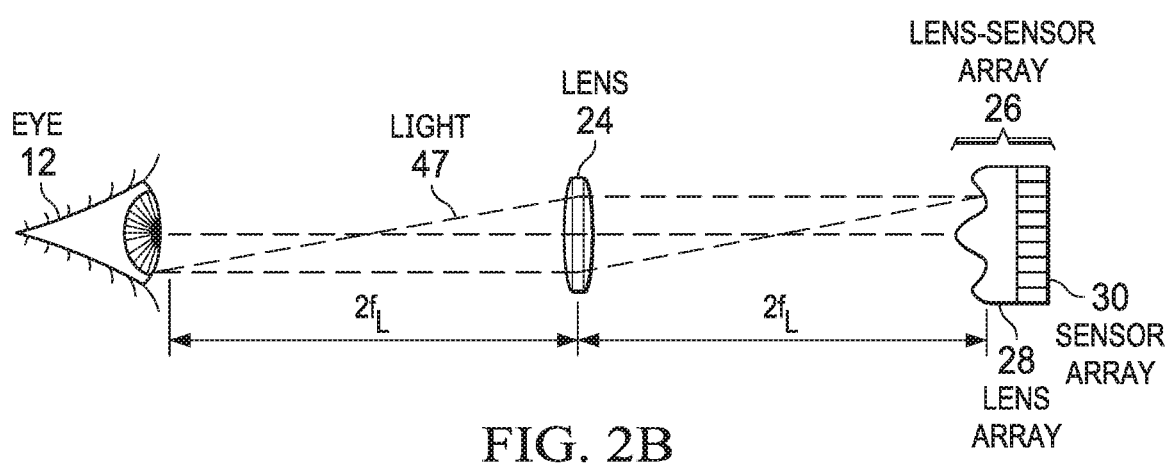
FIG. 2B illustrates imaging the cornea.
Figure 2C:
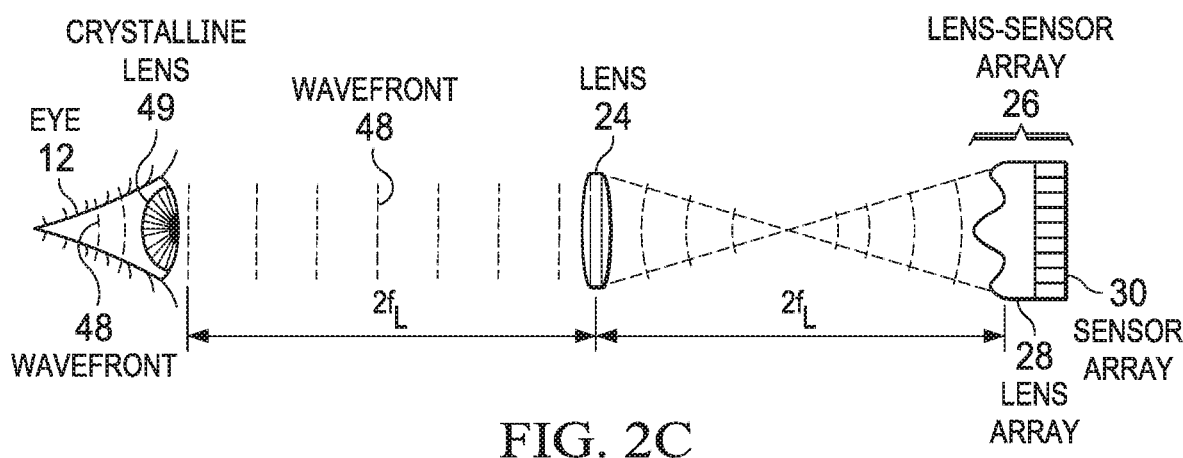
FIG. 2C illustrates imaging the retina.
Figure 2D:
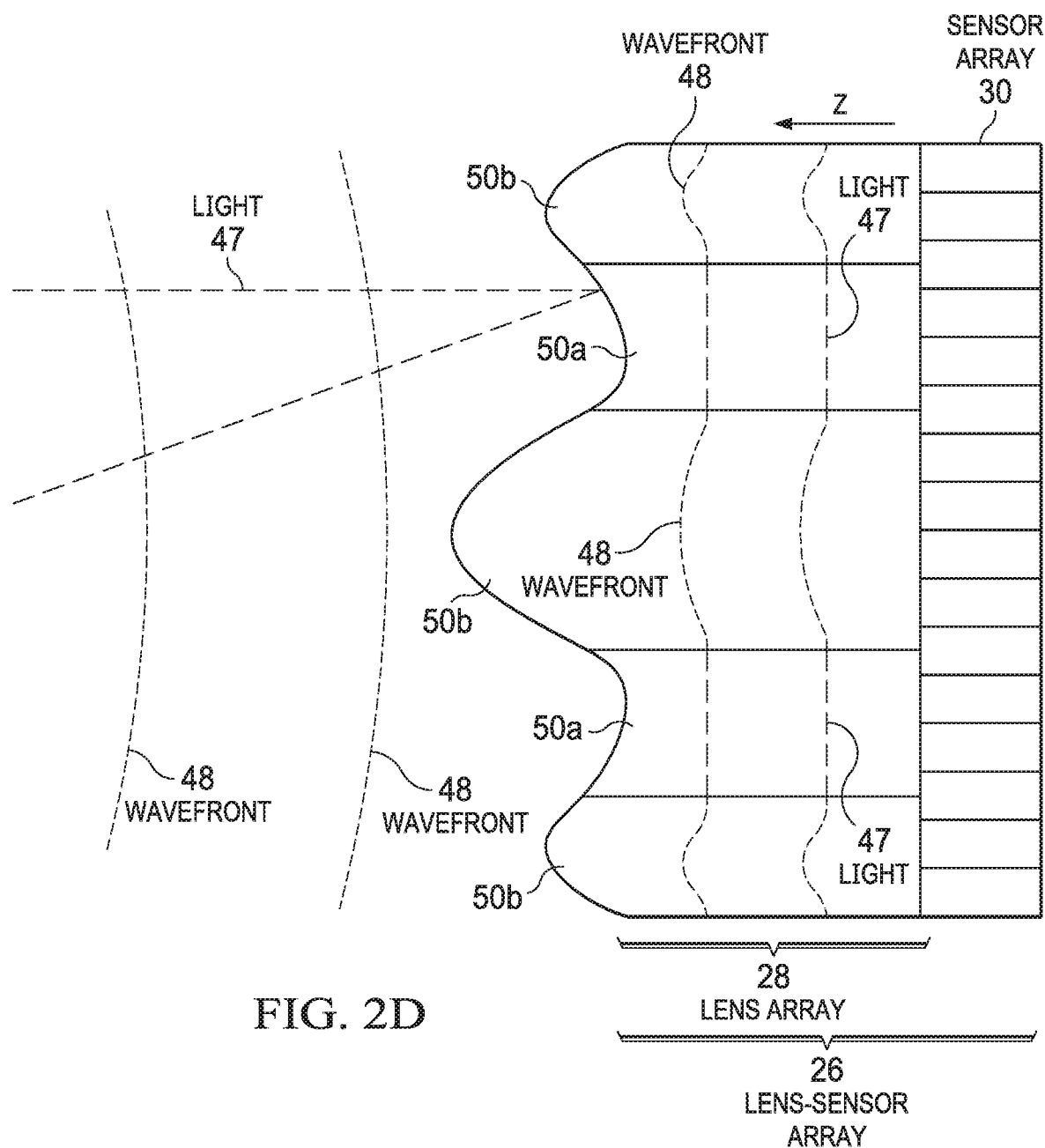
FIG. 2D illustrates the operation of a sensor array that may be used with the system of FIG. 1.

FIGS. 2A to 2D illustrate an example of imaging parts of eye 12 (e.g., the cornea and retina) using system 10 of FIG. 1. FIG. 2A illustrates imaging the cornea and retina. To simplify the explanation, FIG. 2B illustrates imaging the cornea, and FIG. 2C illustrates imaging the retina. FIG. 2D illustrates the operation of sensor array 30 in more detail.

Referring to FIG. 2A, light reflected from eye 12 comprises light reflected from the cornea and light reflected from the retina. Light is reflected from the cornea as light 47, and light is reflected from the retina of eye as wavefront 48. Lens 24, which has focal length $f_L$, transmits the light towards lens-sensor array 26. The distance between the cornea and lens 24 is $2f_L$, and the distance between lens 24 and lens array 28 is $2f_L$.

Referring to FIG. 2B, light 47 from the cornea passes through lens 24 and travels towards lens-sensor array 26. Since the distance between the cornea and lens 24 is $2f_L$, and the distance between lens 24 and lens array 28 is $2f_L$, light 47 is focused at the first section.

Referring to FIG. 2C, wavefront 48 from the retina passes through the crystalline lens 49 of eye 12, which has focal length $f_C$. Wavefront 48 travels through lens 24 towards lens-sensor array 26. Each lenslet of the second section makes a small image of the retina. The lenslets of the second section perform tilt compensation of wavefront 48 and direct light spots towards the sensors of sensor array 26.

Referring to FIG. 2D, lens array 28 comprises first section with first sub-sections 50a and second section with second sub-sections 50b. Light 47 travels through first sub-sections 50a to sensor array 30, and wavefront 48 travels through second sub-sections 50b to sensor array 30. A lenslet of lens array 28 may have any suitable dimensions, e.g., approximately 150 to 300 micrometers (μm) across as measured relative to a plane parallel to sensor array 30, and a thickness T of approximately 3 to 10 millimeters measured in a direction z that is normal to the plane. The lenslets may comprise any suitable material (e.g., a polymer) of any suitable refractive index n (e.g., an index in the range of 1.3 to 1.4, 1.4 to 1.5, and/or 1.5 to 1.6).

In certain embodiments, the first section may be used to image the cornea and other parts of eye 12 near the cornea, e.g., the sclera and iris. To image the cornea, the sensors of sensor array 30 should be at the image plane of lens 24 and lens array 28. The location of sensors relative to lens 24 and/or the focal length $f_1$ of the first section of lenslets may selected to achieve this.

To simplify the explanation, consider a hypothetical situation where lens-sensor array 26 does not include lens array 28. The image plane of lens 24 is at a distance of $2*f_L$ from lens 24, where * represents multiplication and $f_L$ represents the focal length of lens 24, so the sensors should be a distance of $2*f_L$ to capture the image. In contrast to the hypothetical situation, lens-sensor array 26 has lens array 28 with a thickness T and a refractive index n, which moves the image plane a distance of $(n-1)*T$ farther away from lens 24. For example, let $2*f_L=500$ mm, $n=1.4$, and $T=6$ mm. Thus, the image plane is moved a distance of $(1.4-1)*6$ mm=2.4 mm farther away from lens 24.

The location of sensors relative to lens 24 and/or the focal length $f_1$ of the first section of lenslets may selected to position the image plane at the sensors. In certain embodiments, the sensors are placed at the new image plane $(n-1)*T$ farther away from lens 24, and the optical (refractive) power (equal to 1/focal length) of the first section is zero, i.e., the focal length approaches plus or minus infinity. As in the example, the sensors are placed at distance 2.4 mm farther away from lens 24 than they would be in the hypothetical situation without lens array 28.

In other embodiments, the first section of lenslets may have a focal length $f_{1_{lenslet}}$ that places the image plane at the sensors. The appropriate focal length $f_1$ may be calculated using the following thin lens equation:

$$\frac{1}{f_1} + \frac{1}{f_2} = \frac{1}{f_3}$$

where $f_1$ represents the focal length of the system without lens array 28, $f_2$ represents the focal length of the first lenslets of lens array 28, and $f_3$ represents the focal length of the system with lens array 28. As in the example, $f_1$=8.4 mm, and $f_3$=6 mm. Thus, the first section of lenslets have a focal length $f_{1_{lenslet}}$=$f_2$~21 mm.

In yet other embodiments, a combination of the location of sensors relative to lens 24 and the focal length $f_{1_{lenslet}}$ of the first lenslet section of may be selected to position the image plane at the sensors. The location and focal length $f_{1_{lenslet}}$ may be selected according to the thin lens equation.

In certain embodiments, the second section may be used to image the retina and other parts of eye 12 near the retina using wavefront analysis. The second section may include combination lenslets with two focal lengths that operate to generate a plane wavefront directly in front of the lenslets: a focal length $f_A$ and a focal length $f_L$-$f_A$, where $f_L$ represents the focal length of lens 24. Focal length $f_A$ may have any suitable value, e.g., a value in the range of 2 to 4, 4 to 6, 6 to 8, or 8 to 10 mm. Focal length $f_L$-$f_A$ corresponds to a tilt correction for the lenslets, so the second section of lenslets have a focal length $f_A$ with a tilt component.

Figure 3A:
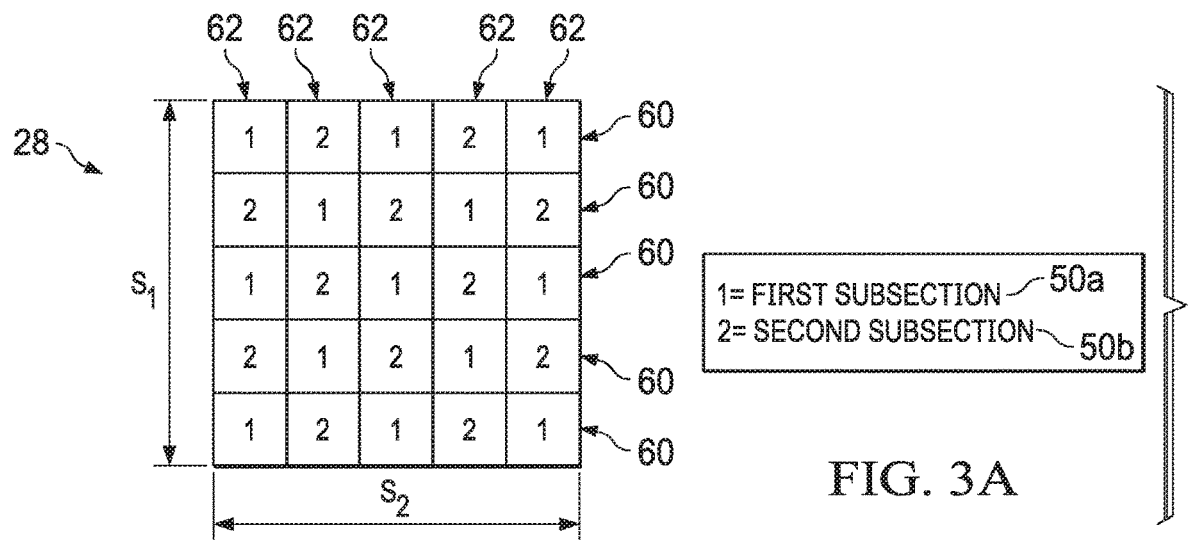
FIG. 3A illustrates an example of a lens array with a chequered pattern that may be used with the system of FIG. 1.
Figure 3B:
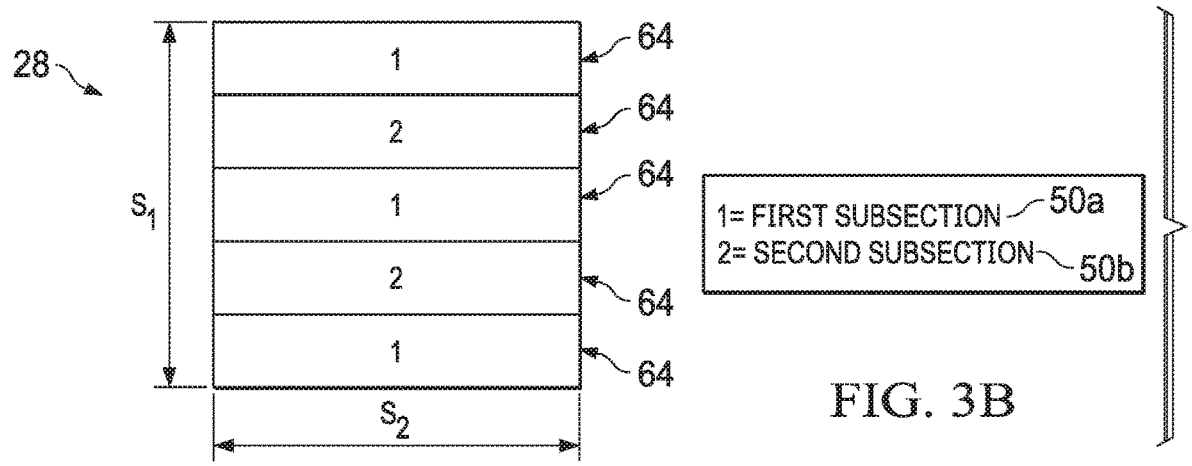
FIG. 3B illustrates an example of a lens array with a striped pattern that may be used with the system of FIG. 1.
Figure 3C:
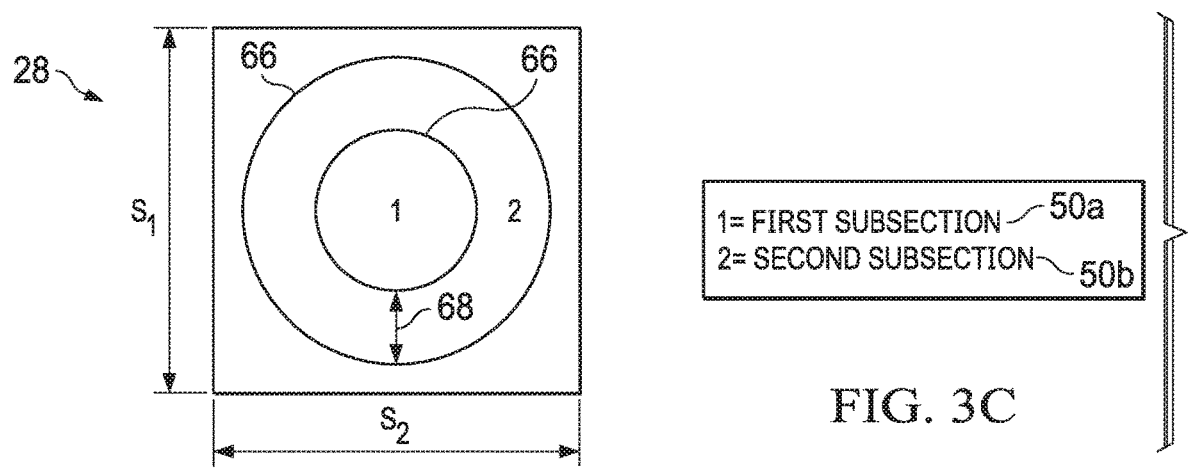
FIG. 3C illustrates an example of a lens array with a concentric annular pattern that may be used with the system of FIG. 1.

FIGS. 3A to 3C illustrate examples of lens array 28 that may be used with system 10 of FIG. 1. Lens array 28 may have any suitable shape and size. In certain embodiments, lens array 28 has a shape and size that is approximately the same as the shape and size of sensor array 30 to allow for disposing (e.g., printing) lens array 28 onto sensor array 30. In the illustrated embodiments, lens array 28 is a rectangle with sides of lengths $S_1$ and $S_2$, which may be equal to each other or not.

Lens array 28 may have any suitable number of first 50*a* and second sub-sections 50*b* of any suitable shape and size. The number of first 50*a* sub-sections may be greater than, less than, or equal to the number of second sub-sections 50*b*. First sub-sections 50*a* may have the same shape and size as the shape and size of the second sub-sections 50*b*, or they may have a different shape or size. One first sub-section 50*a* may have the same shape and size as that of another first sub-section 50*a*, or may have a different shape or size. The same holds for second sub-sections 50*b*.

In certain embodiments, the pattern of sub-sections 50*a-b* (including the number, shape, and size of sub-sections 50*a-b*) may be designed to allow for placement onto sensor array 30. For example, limitations of a printing process may restrict the minimum size of a sub-section 50*a-b*. In certain embodiments, the pattern of sub-sections 50*a-b* may be designed to perform specific tasks. For example, second sub-sections 50*b* that receive wavefront 48 from the retina may be placed in a central area of lens array 28, and first sub-sections 50*a* that receive light 47 from the cornea may be placed in an outer area of lens array 28.

FIG. 3A illustrates an example of lens array 28, where first 50*a* and second sub-sections 50*b* are arranged in a chequered pattern. First 50*a* and second sub-sections 50*b* are arranged in rows 60 and columns 62. In each row 60, each first sub-section 50*a* is adjacent to a second sub-section 50*b*. In each column, each first imaging sub-section 50*a* is adjacent to a second sub-section 50*b*. The pattern may include any suitable number of rows 60 (e.g., 2 to 5, 5 to 10, or greater than 10) and columns 62 (e.g., 2 to 5, 5 to 10, or greater than 10) that allow for placement on sensor array 30. The number of rows 60 may be greater than, equal to, or less than the number of columns 62.

FIG. 3B illustrates an example of lens array 28, where first 50*a* and second sub-sections 50*b* are arranged in a striped pattern. A first sub-section 50*a* is shaped like a first rectangle 64, and a second sub-section 50*b* is shaped like a second rectangle 64 adjacent to the first rectangle. The pattern may include any suitable number of rectangles 64 (e.g., 2 to 5, 5 to 10, or greater than 10) that allows for placement on sensor array 30. The sides of a rectangle 64 may have any suitable lengths and length ratio that allow for placement on sensor array 30. Rectangles 64 may have the same shape and size, or may have different shapes or sizes.

FIG. 3C illustrates an example of lens array 28, where first 50*a* and second sub-sections 50*b* are arranged in a concentric annular pattern. The pattern comprises at least two annular ring shaped sub-sections. A first sub-section 50*a* is shaped like a first annular ring 66, and a second sub-section 50*b* is shaped like a second annular ring 66 concentric with the first annular ring 66. In certain examples, the central sub-section 66 may be a circle. The pattern may include any suitable number of annular rings 66 (e.g., 2 to 5, 5 to 10, or greater than 10) that allows for placement on sensor array 30. An annular ring 66 may have any suitable radial width 68 that allows for placement on sensor array 30.

Figure 4:
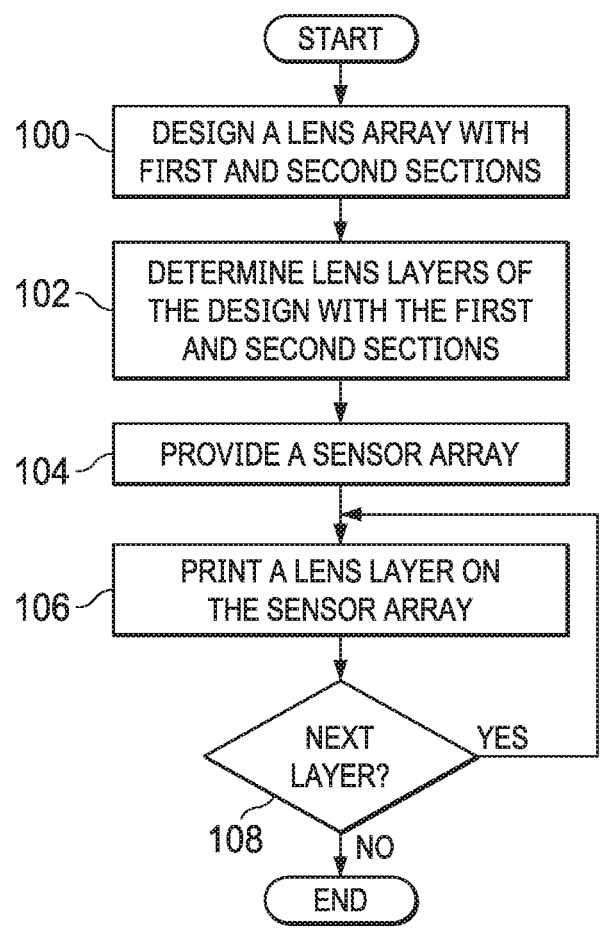
FIG. 4 illustrates an example of a method of making a lens-sensor array that may be used with the system of FIG. 1.

FIG. 4 illustrates an example of a method of making lens-sensor array 26 that may be used with system 10 of FIG. 1. The method begins at step 100, where lens array 28 with first 50*a* and second sections 50*b* is designed. For example, the design may be as described with reference to FIG. 2D.

The lens layers of the design are determined at step 102. A lens layer is a layer that is printed during an additive manufacturing process such that the accumulation of layers results in a lens array that matches the design. In the example of FIG. 2D, one or more of the lens layers include parts that make up the first 50*a* and second sections 50*b*. The layers may have generally the same thickness as measured in the z direction. A first layer may be a layer that is printed directly onto sensor array 30. A next layer is a layer printed on the first layer. Successive layers are printed in a similar manner in the z direction.

Sensor array 30 that serves as a substrate for the additive manufacturing process is provided at step 104. A lens layer is printed on sensor array 30 at step 106. If there is a next layer to print at step 108, the method returns to step 106 to print the layer. If not, the method ends.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as a computer, a microprocessor, or a field programmable gate array (FPGA). Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for imaging parts of an eye, comprising:
   a light source and optics configured to direct light towards a plurality of parts of the eye, the parts reflecting the light;
   a lens configured to transmit the reflected light; and
   a lens-sensor array comprising a lens array disposed onto a sensor array, wherein the lens array is configured to transmit the light from the lens towards the sensor array, the lens array comprising:
      a first section having a plurality of first sub-sections, each first sub-section comprising at least one first lenslet; and
      a second section having a plurality of second sub-sections, each second sub-section comprising at least one second lenslet;
      wherein the first and second sub-sections form a concentric annular pattern including:
         a first sub-section that is shaped like a first annular ring, and wherein the at least one first lenslet in the first sub-section is configured to direct light reflected by a cornea of the eye to the sensor array, and
         a second sub-section that is shaped like a second annular ring concentric with the first annular ring, and wherein the at least one first lenslet in the second sub-section is configured to direct light reflected by a retina of the eye to the sensor array;
   the sensor array further comprising a plurality of sensors configured to:
      detect the light from the lens array; and
      generate a plurality of sensor signals corresponding to the light reflected by the cornea of the eye and the light reflected by the retina of the eye.

2. The system of claim 1, wherein the first section has an optical power of zero.

3. The system of claim 1, wherein the second section has a focal length of 2 to 10 millimeters with a tilt component.

4. A lens-sensor array for imaging parts of an eye, comprising:
   a lens array disposed onto a sensor array;
   the lens array configured to transmit a light from a lens towards the sensor array, the lens array comprising:
      a first section having a plurality of first sub-sections, each first sub-section comprising at least one first lenslet; and
      a second section having a plurality of second sub-sections, each second sub-section comprising at least one second lenslet;
      wherein the first and second sub-sections form a concentric annular pattern including:
         a first sub-section that is shaped like a first annular ring, and wherein the at least one first lenslet in the first sub-section is configured to direct light reflected by a cornea of the eye to the sensor array, and
         a second sub-section that is shaped like a second annular ring concentric with the first annular ring, and wherein the at least one first lenslet in the second sub-section is configured to direct light reflected by a retina of the eye to the sensor array;
   the sensor array further comprising a plurality of sensors configured to:
      detect the light from the lens array; and
      generate a plurality of sensor signals corresponding to the light reflected by the cornea of the eye and the light reflected by the retina of the eye.

5. The lens-sensor array of claim 4, wherein the first section has an optical power of zero.

6. The lens-sensor array of claim 4, wherein the second section has a focal length of 2 to 10 millimeters with a tilt component.

7. A method for making a lens-sensor array for imaging parts of an eye, comprising:
   providing a sensor array as a substrate;
   printing a plurality of lens layers onto the substrate to yield:
      a first section a plurality of first sub-sections, each first sub-section comprising at least one first lenslet; and
      a second section having a plurality of second sub-sections, each second sub-section comprising at least one second lenslet,
      wherein the first and second sub-sections form a concentric annular pattern including:
         a first sub-section that is shaped like a first annular ring, and wherein the at least one first lenslet in the first sub-section is configured to direct light reflected by a cornea of the eye to the sensor array, and
         a second sub-section that is shaped like a second annular ring concentric with the first annular ring, and wherein the at least one first lenslet in the second sub-section is configured to direct light reflected by a retina of the eye to the sensor array.

* * * * *